US008277422B2

(12) United States Patent
Oliver et al.

(10) Patent No.: US 8,277,422 B2
(45) Date of Patent: Oct. 2, 2012

(54) MULTI-CHAMBERED RETRACTABLE SAFETY SYRINGE

(75) Inventors: Richard B. Oliver, Mission Viejo, CA (US); Daniel Thayer, Mission Viejo, CA (US); Jeffrey Smith, Irvine, CA (US); Rex O. Bare, Lake Forest, CA (US)

(73) Assignee: SafeShot Technologies, LLC, Mission Viejo, CA (US)

( * ) Notice: Subject to any disclaimer, the term of this patent is extended or adjusted under 35 U.S.C. 154(b) by 95 days.

(21) Appl. No.: 12/842,885

(22) Filed: Jul. 23, 2010

(65) Prior Publication Data

US 2012/0022447 A1   Jan. 26, 2012

(51) Int. Cl.
*A61M 5/00* (2006.01)

(52) U.S. Cl. .................. 604/218; 604/110; 604/187

(58) Field of Classification Search .......... 604/110, 604/121, 128, 129, 191, 218, 222, 229, 187, 604/221

See application file for complete search history.

(56) References Cited

U.S. PATENT DOCUMENTS

| | | |
|---|---|---|
| 4,766,908 A | 8/1988 | Clement |
| 4,838,869 A | 6/1989 | Allard |
| 4,950,241 A | 8/1990 | Ranford |
| 4,966,593 A | 10/1990 | Lennox |
| 5,019,043 A | 5/1991 | Pastor et al. |
| 5,085,640 A | 2/1992 | Gibbs |
| 5,195,985 A | 3/1993 | Hall |
| 5,211,630 A | 5/1993 | Schmahmann |
| 5,215,015 A | 6/1993 | Iida et al. |
| 5,215,533 A * | 6/1993 | Robb ............................ 604/195 |
| 5,226,893 A | 7/1993 | Kayser |
| 5,334,155 A | 8/1994 | Sobel |
| 5,336,185 A | 8/1994 | Lynch et al. |
| 5,344,403 A | 9/1994 | Lee |
| 5,385,551 A | 1/1995 | Shaw |
| 5,389,076 A | 2/1995 | Shaw |
| 5,423,758 A | 6/1995 | Shaw |
| 5,578,011 A | 11/1996 | Shaw |
| 5,578,015 A | 11/1996 | Robb |
| 5,601,534 A | 2/1997 | Turner |
| 5,632,733 A | 5/1997 | Shaw |
| 5,658,257 A | 8/1997 | Ryles |
| 5,681,292 A | 10/1997 | Tober et al. |
| 5,868,713 A | 2/1999 | Klippenstein |
| 5,964,735 A | 10/1999 | Alexander |
| 5,971,964 A | 10/1999 | Donaldson |
| 6,010,486 A | 1/2000 | Carter et al. |
| 6,015,438 A | 1/2000 | Shaw |

(Continued)

*Primary Examiner* — Nicholas Lucchesi
*Assistant Examiner* — Leah Stohr
(74) *Attorney, Agent, or Firm* — K&L Gates LLP

(57) ABSTRACT

A retractable safety syringe may have a needle, needle holder, syringe body, and a plunger assembly. A proximal portion of the body and a piston of the plunger may define a vacuum chamber. The plunger assembly may comprise a distal piston and a proximal piston, with an intermediate chamber disposed between the two plungers. A vent through the syringe body pneumatically connects ambient air and the intermediate chamber allowing air to escape out of the intermediate chamber when a plunger assembly traversed toward the engaged position and allow air to be introduced into the intermediate chamber. A retraction force may be created by the vacuum chamber by traversing the plunger assembly to the engaged position. At the engaged position, the distal piston may engage the needle holder and the retraction force may retract the needle holder and needle into the syringe body to prevent accidental needle pricking and needle reuse.

20 Claims, 5 Drawing Sheets

U.S. PATENT DOCUMENTS

| | | |
|---|---|---|
| 6,033,385 A | 3/2000 | Liu |
| 6,036,674 A | 3/2000 | Caizza et al. |
| 6,050,977 A | 4/2000 | Adams |
| 6,090,077 A | 7/2000 | Shaw |
| 6,193,695 B1 | 2/2001 | Rippstein, Jr. |
| 6,368,303 B1 | 4/2002 | Caizza |
| 6,413,236 B1 | 7/2002 | Van Dyke |
| 6,458,105 B1 | 10/2002 | Rippstein, Jr. |
| 6,632,198 B2 | 10/2003 | Caizza |
| 6,712,787 B1 | 3/2004 | Dysarz |
| 6,752,798 B2 | 6/2004 | McWethy et al. |
| 6,840,291 B2 | 1/2005 | Caizza et al. |
| 6,953,449 B2 | 10/2005 | Huang |
| 6,986,756 B2 | 1/2006 | Pelkey et al. |
| 7,104,970 B2 | 9/2006 | Chen |
| 7,118,552 B2 | 10/2006 | Shaw et al. |
| 7,147,621 B2 | 12/2006 | Kiehne |
| 7,220,247 B2 | 5/2007 | Shaw et al. |
| 7,572,247 B2 | 8/2009 | Smith et al. |
| 2001/0053886 A1 | 12/2001 | Caizza |
| 2002/0193736 A1 | 12/2002 | Kiehne |
| 2003/0023205 A1 | 1/2003 | Botich et al. |
| 2003/0212362 A1 | 11/2003 | Roser |
| 2004/0024357 A1 | 2/2004 | Pelkey et al. |
| 2004/0116857 A1 | 6/2004 | Kiehne |
| 2006/0089593 A1 | 4/2006 | Landau et al. |
| 2006/0089594 A1 | 4/2006 | Landau |
| 2006/0178625 A1 | 8/2006 | Lim et al. |
| 2006/0253074 A1* | 11/2006 | Thayer .......................... 604/110 |
| 2006/0264840 A1 | 11/2006 | Thayer |
| 2007/0000556 A1 | 1/2007 | Smith et al. |
| 2007/0066936 A1 | 3/2007 | Lam |
| 2007/0255212 A1 | 11/2007 | Smith et al. |
| 2007/0260180 A1 | 11/2007 | Smith et al. |
| 2007/0260181 A1 | 11/2007 | Smith et al. |
| 2008/0027381 A1 | 1/2008 | Smith et al. |

* cited by examiner

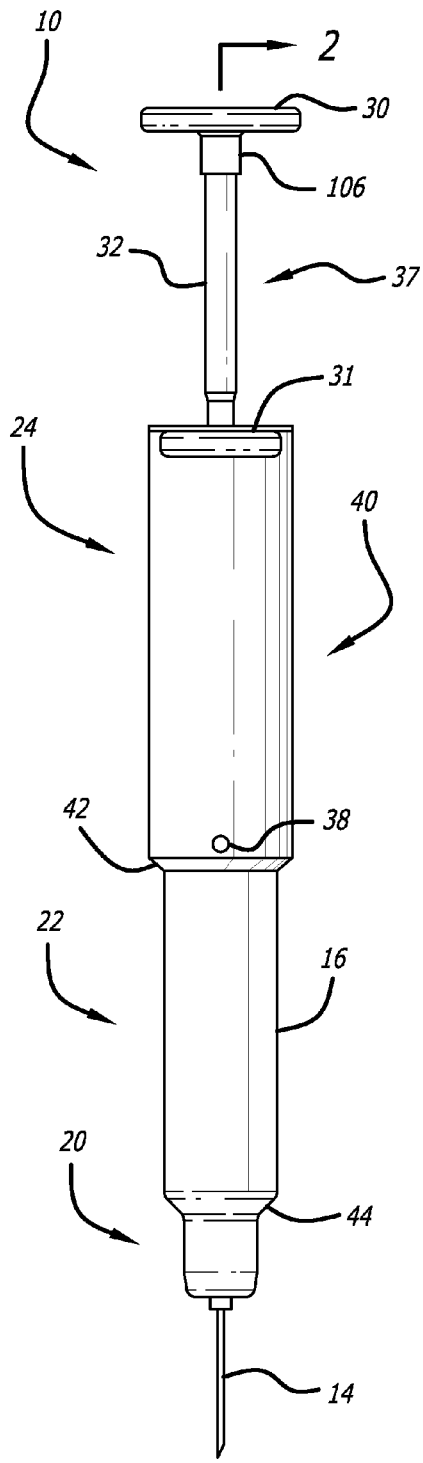
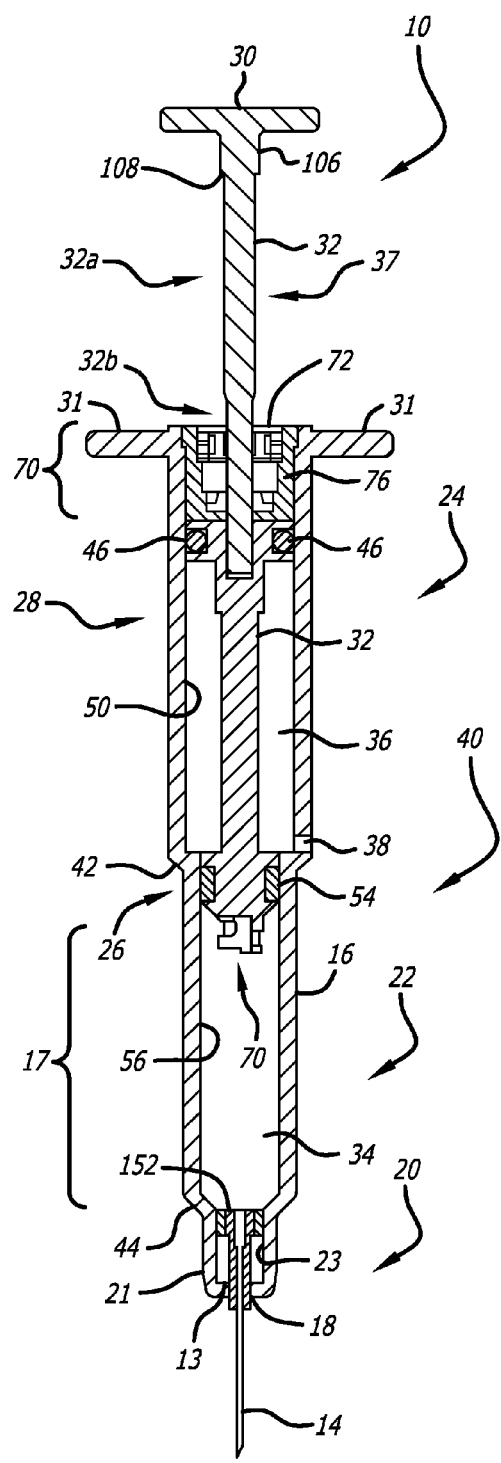
FIG. 1
FIG. 2

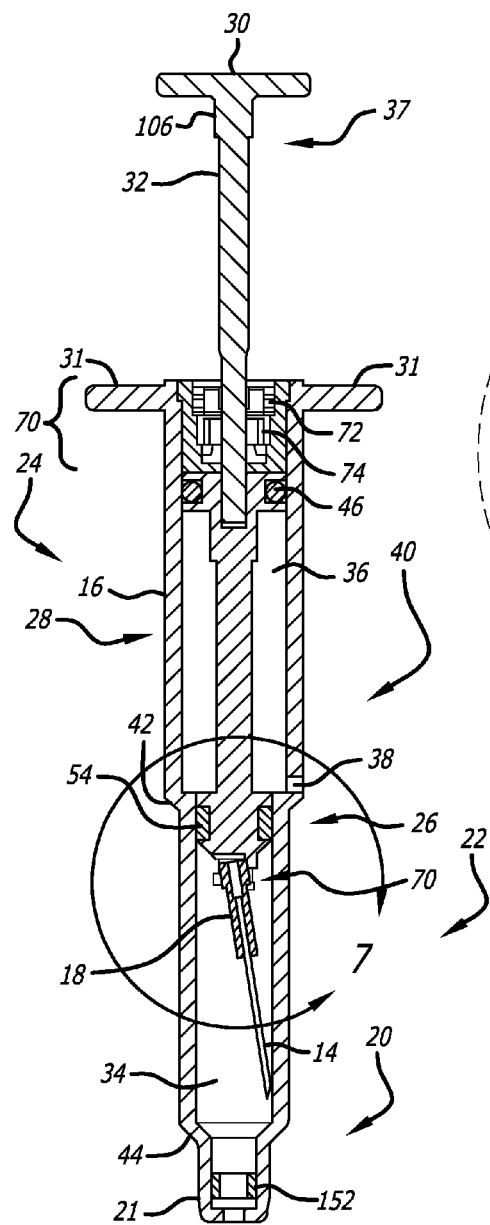
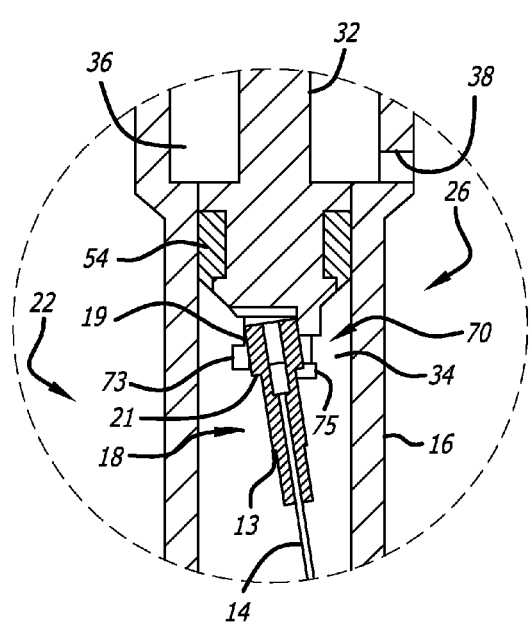
FIG. 6
FIG. 7

MULTI-CHAMBERED RETRACTABLE SAFETY SYRINGE

BACKGROUND

The present invention generally relates to syringes, including small volume (e.g., about 1 cc or less) retractable safety syringes.

In recent years, the public (e.g., medical personnel and healthcare providers, drug addicts, drug users, and the like) has become increasingly aware of the health hazards associated with needle reuse and accidental needle prickings. For example, at least twenty blood-borne pathogens may be transmitted by the reuse of needles or accidental needle prickings. For example, these blood borne pathogens may include and are not limited to Human Immunodeficiency Virus (HIV), Acquired Immunodeficiency Syndrome (AIDS), Hepatitis B, Hepatitis C, syphilis, malaria, tuberculosis, and herpes. Despite the awareness of the risk of needle reuse and accidental needle prickings, at least 36 percent of HIV/AIDS cases and more than 50 percent of Hepatitis B and Hepatitis C cases in the United States may be linked to the sharing of needles among drug addicts. Accordingly, there is a need to curb the practice of sharing needles among drug addicts.

The problem of needle sharing or needle reuses is further amplified when viewed in relation to the world population. For example, approximately 30 percent of reported HIV/AIDS cases in Brazil, Chile, Uruguay, Paraguay and Argentina are directly related to the sharing of contaminated needles among drug addicts. Approximately 70 percent of the HIV cases reported in China are directly linked to the sharing of contaminated needles. In eastern European countries, 80 percent of injection drug addicts admit to sharing contaminated needles. Approximately 43 percent of HIV/AIDS cases reported in Poland and Yugoslavia are linked to the sharing of contaminated needles among drug addicts.

Accidental needle prickings also pose a threat to healthcare workers. In particular, approximately one million accidental needle prickings are reported by healthcare workers annually. However, it is believed that at least three million accidental needle prickings occur each year, of which about two million are unreported. Various studies estimate that out of all the accidental needle pricking injuries that occur to nurses, approximately 40 percent to 53 percent go unreported. Various studies also estimate that out of all the needle pricking injuries that occur to laboratory technicians, approximately 92 percent go unreported. Various studies further estimate that out of all the needle pricking injuries that occur to physicians, approximately 70 percent to 95 percent go unreported.

In 1997, the Center for Disease Control and Prevention (CDC) sponsored a study that found that approximately 76 percent of needle pricking injuries could be avoided by using safety needles. Presently, there are at least 250 types of safety syringes. Unfortunately, the retractable safety syringes that currently exist have been criticized for various problems associated in operating the retractable safety syringe and its ineffectiveness.

One type of safety syringe is a vacuum assisted safety syringe wherein the needle of the syringe is retracted into a syringe body after a piston engages a needle holder due to a retraction force of a variable vacuum compartment. The retraction force of the variable vacuum compartment is a function of the surface area of the piston as it is traversed from a retracted position to an engaged position. If the variable vacuum compartment is not sufficiently large, then the retraction force of the variable vacuum compartment may not be sufficient to withdraw the needle holder and needle into the syringe body. This problem is particularly pronounced when the retractable safety syringe has a small variable fluid chamber of about 1 cc or less. Small variable fluid chambers require a syringe body having a small diameter. Correspondingly, the variable vacuum compartment is also small limiting its maximum potential retraction force. If the retraction force of the variable vacuum compartment is not greater than a force required to traverse the needle holder and needle into the retractable safety syringe, then the needle will still be exposed outside of the syringe body thereby possibly pricking a medical professional or allowing a drug addict to reuse the needle.

Accordingly, there is a need in the art for an improved safety syringe.

SUMMARY

In accordance with various embodiments, a retractable safety syringe may have a syringe body defining a distal portion, an intermediate portion, and a proximal portion. The retractable safety syringe may also have a proximal seal located in the proximal portion of the syringe body and a plunger assembly disposed within the syringe body. The plunger assembly may have a shaft, a distal piston, and a proximal piston. The plunger assembly may be traverseable between a refracted position and an engaged position. The retractable safety syringe may also have a needle coupled to a needle holder. The needle holder may be removeably engageable to the distal portion of the syringe body and engageable to the distal piston when the plunger assembly is traversed to the engaged position. The retractable safety syringe may also have a fluid chamber disposed within the syringe body. The fluid chamber may be located distally from the distal piston and have a distal and proximal end. The proximal end of the fluid chamber may be sealed and the fluid chamber may be in fluid communication with the needle through the distal end of the fluid chamber. The fluid chamber may be configured to be reduced in volume as the plunger assembly is traversed towards the engaged position. The retractable safety syringe may also have a vacuum chamber disposed within the syringe body. The vacuum chamber may be located intermediate the proximal piston and the proximal seal. The vacuum chamber may be configured to provide a vacuum force on the proximal piston in a direction from the syringe body distal portion toward the syringe body proximal portion upon movement of the plunger assembly toward the syringe body distal portion responsive to the distal translation of the plunger assembly. The retractable safety syringe may also have an intermediate chamber disposed within the syringe body. The intermediate chamber may be located intermediate the distal piston and the proximal piston. The intermediate chamber may have an air-passage vent connecting a volume external to the syringe body to the intermediate chamber when the plunger assembly is traversed between the retracted position and the engaged position.

In accordance with another embodiment, a retractable safety syringe may have a syringe body defining a distal portion, an intermediate portion, and a proximal portion. The distal portion may have a first outer diameter, the intermediate portion may have a second outer diameter, and the proximal portion may have a third outer diameter. The first outer diameter may be less than the second outer diameter and the second outer diameter may be less than the third outer diameter. The retractable safety syringe may also have a needle coupled to a needle holder and the needle holder may be removeably engageable to the distal portion of the syringe body. The retractable safety syringe may also have an attachment base attached to the proximal portion of the syringe body and a plunger assembly having a proximal piston and a distal piston. The proximal piston may traverse the proximal portion when the plunger assembly is traversed between a retracted position and an engaged position. The distal piston may traverse the intermediate portion when the plunger assembly is traversed between the retracted position and the engaged position. The retractable safety syringe may also have a distal variable volume fluid chamber disposed between the needle and the distal piston and an intermediate variable volume chamber disposed between the distal piston and the proximal piston. The intermediate variable volume chamber may have a vent connecting the intermediate variable volume chamber to a space external the syringe body. The retractable safety syringe may also have a proximal variable volume vacuum chamber disposed between the distal piston and the attachment base.

In accordance with another embodiment, a method of operating an automatically retracting syringe may include receiving a syringe having a syringe body having first, second, and third cavities. The syringe may also have a needle coupled to a needle holder that is removeably engaged to the syringe body. The syringe may also have a plunger assembly having distal and proximal pistons with the plunger assembly disposed within the syringe body in a retracted position. The syringe may also have a vacuum chamber within the syringe body configured to urge the plunger toward the retracted position. The method of operating the automatically retracting syringe may also include depressing a thumb platform to traverse the piston assembly toward a distal portion of the syringe during an injection stroke and expelling air from the second cavity to a space external the syringe body through a vent. The method may also include inducing a gradually increasing biasing force on the proximal piston of the plunger assembly via the vacuum chamber to urge the piston assembly back toward the retracted position and engaging the distal piston to the needle holder upon completion of the injection stroke. The method may also include disengaging the needle holder from the syringe body, removing thumb pressure on the thumb platform, and traversing the needle holder and the needle into the syringe body under the biasing force.

BRIEF DESCRIPTION OF THE DRAWINGS

The present invention will be more readily understood from a detailed description of example embodiments taken in conjunction with the following figures:

FIG. 1 is a side view of a retractable safety syringe in accordance with one non-limiting embodiment.

FIG. 2 is a cross-sectional view of the retractable safety syringe of FIG. 1.

FIGS. 4-6 are cross-sectional views of the retractable safety syringe of FIG. 1 during various stages of operation.

FIG. 7 illustrates an enlarged view of a portion of FIG. 6.

DETAILED DESCRIPTION OF EXAMPLE EMBODIMENTS

Figure 3:
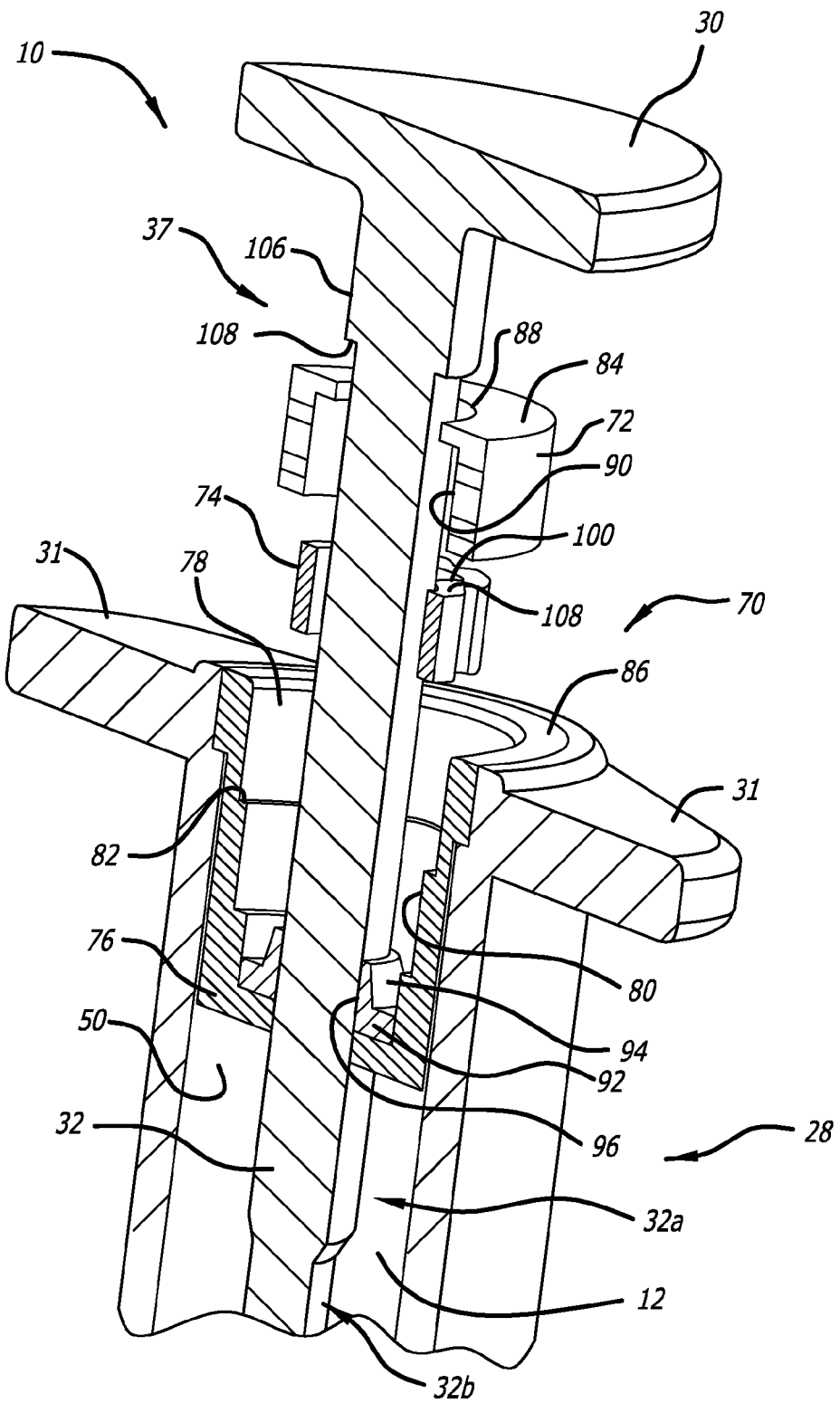
FIG. 3 is a cross sectional perspective view of the distal end of the retractable safety syringe with an exploded view of a braking mechanism in accordance with one non-limiting embodiment.

It will be appreciated that the terms "proximal" and "distal" may be used throughout the specification with reference to a medical professional or user utilizing a syringe to deliver medication to a patient. The term "proximal" refers to the portion of the syringe closest to the medical professional or user and the term "distal" refers to the portion located furthest from the medical professional or user. It will be further appreciated that for conciseness and clarity, spatial terms such as "vertical," "horizontal," "up," and "down" may be used herein with respect to the illustrated embodiments. However, syringes may be used in many orientations and positions, and these terms are not intended to be limiting and absolute.

FIGS. 1-2 illustrate a retractable safety syringe 10 in accordance with one non-limiting embodiment. FIG. 1 is a side view of the retractable safety syringe 10. FIG. 2 is a cross sectional view of the retractable safety syringe of FIG. 1 taken along Line 2-2. The retractable safety syringe 10 has a vacuum chamber 12 (FIG. 5) that creates a retraction force to retract a needle 14 of the retractable safety syringe 10 within the retractable safety syringe 10 so as to prevent accidental needle pricking and needle reuse. Although the discussion provided herein regarding the retractable safety syringe 10 is made in relation to small volume syringes (e.g., about 1 cc or less), for which the example embodiment is particularly well-suited, it is also contemplated that the various aspects of the retractable safety syringe 10 may also be variously embodied and employed in safety syringes having larger volumes (e.g., 1 cc or more).

The retractable safety syringe 10 may have a syringe body 16 defining a distal portion 20, an intermediate portion 22, and a proximal portion 24. The intermediate portion 22 may define a fluid chamber 34 fillable with fluidic medication. While the example shown is not a pre-filled syringe, it will be appreciate that alternative examples may be provided for use in a pre-filled syringe application. A needle holder 18 may be removably engaged to the distal portion 20 of the syringe body 16. A needle 14 may be fixedly engaged to the needle holder 18 and protrude coaxially out of the distal portion 20 of the syringe body 16. The fluid chamber 34 is in fluid communication with the needle 14 through the distal end of the fluid chamber 34. The retractable safety syringe 10 may also have a plunger assembly 37. The plunger assembly 37 may also having a distal piston 26 and a proximal piston 28 disposed along a rigid shaft 32. In various embodiments, the rigid shaft 32 may having a plurality of components assembled together to form the shaft. The proximal piston 26 may have a punch 70 distally protruding toward the needle holder 18. The plunger assembly 37 is traversable within the syringe body 16 between a retracted position and an engaged position. Generally, the retracted position is when the distal piston 26 and the proximal piston 28 are closer to the proximal portion 24 of the syringe body 16 than the distal portion 20 of the syringe body 16. But, the retracted position may include situations when the distal piston 26 does not contact the needle holder 18 and the distal piston 26 and the proximal piston 28 are closer to the distal portion 20 of the syringe body 16 than the proximal portion 24 of the body 16. The engaged position is when the distal piston 26 is in contact with the needle holder 18 and engaged to the needle holder 18 (see FIG. 5). The rigid shaft 32 may extend out of the syringe body 16 through the proximal portion 24 of the syringe body 16 and may be coaxially aligned with the syringe body 16. A portion of the rigid shaft 32 may also extend between and couple the distal piston 26 and the proximal piston 28. A thumb platform 30 may be attached to the proximal portion of the rigid shaft 32. The thumb platform 30 may be operative to traverse the plunger assembly 37 between the retracted position and the engaged position. The retractable safety syringe 10 may also finger platforms 31 extending laterally from the proximal portion 24.

A wedge element 152 may be positioned between the needle holder 18 and the distal portion 20 to form an airtight and fluid tight seal therebetween. In particular, the distal portion 20 of the body 16 may have a cylindrical nub 21. The needle holder 18 may a corresponding configuration as an inner surface 23 of the cylindrical nub 21. The needle holder 18 may have a lip 13 (see FIGS. 2 and 7) to engage the distal portion 20 such that the needle holder 18 is not pushed out the distal portion 20 of the body 16 as a wedge element 152 is traversed to the releasing position (discussed below).

The retractable safety syringe 10 may also define an intermediate chamber 36 positioned intermediate the distal piston 26 and the proximal piston 28. The intermediate chamber 36 may define a vent 38 allowing air to flow into the intermediate chamber 36 and flow out of the intermediate chamber 36, as discussed in more detail below. While vent 38 is illustrated as a bore, it is to be appreciated that the vent 38 may be a variety of shapes and may be located on the retractable safety syringe 10 in a variety of positions. For example, in some embodiments, the vent 38 may be a series of slits arranged around a circumference of the syringe body 16. In other embodiments, the vent 38 may be a bore that is larger or small in diameter than the illustrated embodiment. In various embodiments, the vent 38 may be triangular, quadrangular (e.g., square, rectangle, rhomboidal), circular, oval, or any combination, for example. In any event, the vent 38 allows a pressure inside the intermediate chamber 36 to equalize to the pressure in a volume 40 external to the retractable safety syringe 10, e.g., the ambient air where the syringe is used.

Still referring to FIGS. 1 and 2, the distal portion 20, the intermediate portion 22, and the proximal portion 24 may each have an elongate cylindrical configuration, each having an inner and an outer diameter. In the illustrated embodiment, the outer diameters of the various portions of the syringe body 16 may vary. For example, the outer diameter of the proximal portion 24 may be larger than the outer diameter of the intermediate portion 22, which is larger than the outer diameter of the distal portion 20. Similarly, the inner diameters of the various portions of the syringe body 16 may vary. For example, the inner diameter of the proximal portion 24 may be larger than the inner diameter of the intermediate portion 22, which is larger than the inner diameter of the distal portion 20. The syringe body 16 may have a proximal reducing portion 42 positioned intermediate the proximal portion 24 and the intermediate portion 22. The syringe body 16 may also have a distal reducing portion 44 positioned intermediate the intermediate portion 22 and the distal portion 20. By stepping down the diameters of the various portions, the fluid chamber 34 may be suitably sized to receive and dispense small volumes of medication (e.g., less than 1 cc), while the vacuum chamber 12 is large enough to generate a sufficient retraction force. As is to be appreciated, in some embodiments, multiple portions of the syringe body 16 may have similar inner and/or outer diameters. For example, in one embodiment, the outer diameter of the proximal portion 24 is similar to the outer diameter of the intermediate portion 22. Furthermore, while the illustrated embodiments of the various portions of the retractable safety syringe 10 are cylindrical shapes having circular cross-sections, it is appreciated that the various portions of the retractable safety syringe 10 are not so limited. Instead, each of the distal portion 20, intermediate portion 22, and proximal portion 24 may each be any suitable shape, where its cross-section defines an oval, triangular, square, rectangular, pentagonal, hexagonal, or any other suitable bounded shape, such as a shape having multiple facets. In such embodiments, the distal piston 26 and the proximal piston 28 may define a corresponding bounded shape. In one embodiment, for example, the distal portion 20 and intermediate portion 22 each have a circular cross-section, while the proximal portion 24 has an oval cross-section.

Various portions of the body 16 may be transparent to allow viewing of the fluidic medication by the user. Furthermore, a marked portion 17 may also have volume markings, or other indicia, to indicate volume levels within the fluid chamber 34. The aspect ratio (i.e., the ratio of the height to the width) of the fluid chamber 34 for any particular retractable safety syringe 10 may vary based on the intended volume of medication to be dispensed. For neonatal embodiments, for example, the aspect ratio of the fluid chamber 34 may be configured to provide the proper resolution to dispense medication in extremely small dosages (e.g., less than 1 cc, or less than 0.5 cc). In other embodiments, the aspect ratio of the fluid chamber 34 may be configured to dispense medication in larger dosages (e.g., more than 1 cc).

The proximal piston 28 may have an outer diameter similar to the inner diameter of the proximal portion 24. The proximal piston 28 may have a first seal 46 which engages an outer surface of the proximal piston 28 and an inner surface 50 of the proximal portion 24. In one embodiment, the first seal 46 is an o-ring. In other embodiments, the first seal 46 may be integral with the proximal piston 28, such as a molder wiper seal, for example. The first seal 44 may form an airtight seal between the proximal piston 28 and the inner surface 50 of the proximal portion 24. The first seal 44 may traverse along the inner surface 50 of the proximal portion 24 as the plunger assembly 37 is traversed between the retracted position and the engaged position.

The distal piston 26 may have an outer diameter similar to the inner diameter of the intermediate portion 22. The distal piston 26 may have a second seal 54 which engages an outer surface of the distal piston 26 and an inner surface 56 of the intermediate portion 22. The second seal 54 may form a watertight and an airtight seal between the distal piston 26 and the inner surface 56 of the intermediate portion 22. The second seal 54 may traverse along the inner surface 56 of the intermediate portion 22 as the plunger assembly 37 is traversed between the retracted position and the engaged position.

In various embodiments, the retractable safety syringe 10 may further have a braking mechanism 70 disposed at the proximal portion 24 that holds the plunger assembly 37 in place at any position between the retracted position and a filling position prior to engagement of the distal piston 26 with the needle holder 18. The filling position when the plunger assembly 37 is between the engaged position and the retracted position and the distal piston 26 is closely adjacent the needle holder 18. By way of example and not limitation, the filling position may be when the distal piston 26 is in contact with the needle holder 18 but not engaged to the needle holder 18. FIG. 3 is a cross sectional view of the distal end of the retractable safety syringe 10 illustrating an exploded view of the braking mechanism 70 in accordance with one non-limiting embodiment. With reference to FIGS. 2 and 3, the braking mechanism 70 permits the retractable safety syringe 10 to be operated in a substantially similar manner to prior art non-retracting conventional syringes except that the syringe 10 automatically retracts the needle 14 into the body 16 immediately after fluidic medication has been injected into a patient or user. In prior art non-retracting safety syringes, the piston does not traverse back toward the retracted position when thumb pressure is released from the thumb platform. The reason is that prior art non-retracting safety syringes do not have a retraction force acting on the piston. In the illustrated embodiment, the plunger assembly 37 does not traverse back toward the retracted position when thumb pressure is released from the thumb platform 30 because of the braking mechanism 70. The braking mechanism 70 of retractable safety syringe 10 counteracts the retraction force of the vacuum chamber 12 such that the needle 14 does not automatically retract when thumb pressure is released from a thumb platform 30.

The braking mechanism 70 may have a cover 72 and a brake member 74 that are engaged to an attachment base 76. The attachment base 76 may define an inner that has a stepped configuration. An upper step 78 may have a larger inner diameter compared to an inner diameter of a lower step 80. The upper step 78 and the lower step 80 may be joined to each other via a lip 82. The cover 72 may have an outer diameter sized to fit the upper step 78. Also, a top surface 84 of the cover 72 may be flush with a top surface 86 of the attachment base 76. The cover 72 may be fixedly attached to the attachment base 76 via sonic welding, adhesive and other joining methods known in the art. The attachment base 76 may be fixedly attached to the proximal portion 24 using any suitable joining technique known in the art, such as spin welding, for example. The cover 72 may have a through-hole 88 through which the shaft 32 may be disposed and slidingly traversed. An inner surface 90 of the cover 72 may have an inner diameter that is smaller than the inner diameter of the lower step 80.

The brake member 74 may be disposed and frictionally engaged to the cover 72. The brake member 74 may be split into two or more pieces. In one embodiment, the brake member 74 is split into two pieces that are mirror configurations of each other. When the brake member 74 is disposed in the cover 72, an outer diameter of the brake member 74 may be equal to or slightly greater than the inner diameter of the inner surface 90 of the cover 72. In this manner, the brake member 74 frictionally engages the cover 72 and the inner surface 90 of the cover 72 biases the brake member 74 inwardly toward the shaft 32. The amount of inward bias may be pre-set by changing the relative sizes of the inner diameter of the cover 72 and the outer diameter of the brake member 74.

The attachment base 76 may also house a shaft seal 92. The shaft seal 92 may have a longitudinal flange 94 defining a through-hole 96 through which the shaft 32 may be disposed and slidingly traversed. The shaft seal 92 forms an airtight seal with the shaft 32 in order to maintain a vacuum in the vacuum chamber 12 when the proximal piston 28 is traversed distally from the attachment base 76. The shaft 32 may have different outer diameters for different portions. For example, the shaft 32 may have a wide portion 32a and a narrow portion 32b. The longitudinal flange 94 of the shaft seal 92 may flex to expand or contract the through-hole 96 in order to maintain contact with the shaft 32. Furthermore, as the various portions of the shaft 32 is slidingly traversed past the brake member 74, the brake member will exert more breaking (e.g., frictional) force on the wide portion 32a as compared to the narrow portion 32b.

When the brake member 74 is disposed in the cover 72, the brake member 74 is in a braking position. At the braking position, the brake member 74 may have a plurality of fingers or projections 100 that inwardly protrude toward the shaft 32. The inner surface 88 of the cover 72 biases the projections 100 inwardly, and the projections 100 press against the outer surface of the shaft 32 inducing a frictional force between the projections 100 of the brake member 74 and the outer surface of the shaft 32. Alternatively, it is also contemplated that the brake member 74 may have a cylindrical inner surface. The entire inner surface of the brake member 74 may contact or press against the outer surface of the shaft 32. Accordingly, it is contemplated that the friction surface of the brake member 74 that presses against the outer surface of the shaft 32 may have other configurations to change the amount of inward bias. It is also contemplated the amount of friction force between the brake member 74 and the outer surface of the shaft 32 may be varied to meet the requirements of the syringe. For example, the inner diameter of the inner surface 90 of the cover 72 may be reduced so as to further bias the projections 100 against the outer surface of the shaft 32. The friction force between the brake member 74 and the shaft 32 may also be varied by changing the material of the brake member 74 and the shaft 32 or having different finishes at the interface of the outer surface of the shaft 32 and the friction surface of the brake member 74. During operation, when the brake member 74 is at the braking position (see FIGS. 2 and 4), the friction force between the projections 100 of the brake member 74 and the shaft 32 is less than the friction force between the brake member 74 and the cover 72. In this manner, the brake member 74 is not dislodged out of the cover 72 and within the lower step 80 (e.g., released position) as the plunger assembly 37 is traversed toward the filling position or engaged position. The shaft 32 may slide against the projections 100 of the brake member 74 as the plunger assembly 37 is traversed between the refracted position and the engaged position without the brake member 74 being dislodged from the braking position due to the frictional forces of the projections 100 of the brake member 74 and the shaft 32 being less than the frictional forces of the brake member 74 and cover 72.

The brake member 74 is traversable between the braking position and a released position. When the brake member 74 is traversed to the released position (see FIGS. 5-6), the brake member 74 is disposed within the lower step 80 of the interior cavity of the attachment base 76. The inner surface 90 of the cover 72 no longer biases the projections 100 inwardly to press the projections 100 of the brake member 74 against the shaft 32 creating the frictional force that counteracts the retraction force of the vacuum chamber 12. At the released position, the brake member 74 is loose because the lower step 80 defines a larger volume and the brake member 74 such that the brake member 74 falls apart, or otherwise expands, when disposed within the lower step 80. The projections 100 do not press against the outer surface of the shaft 32 and does not produce any counteracting forces such that the plunger assembly 37 may be freely retracted toward the retracted position when the user releases the thumb platform 30.

To traverse the brake member 74 from the braking position to the released position, the plunger assembly 37 may be formed with a ram 106 which initially contacts an upper surface 109 (see FIG. 3) of the brake member 74 and pushes the brake member 74 out of the cover 72 and within the lower step 80. More particularly, when the plunger assembly 37 is traversed toward the engaged position, a lower surface 108 of the ram 106 contacts the upper surface 109 of the brake member 74. As the plunger assembly 37 is further traversed to the engaged position, the ram 106 continues to push downwardly on the brake member 74 urging the brake member 74 off of the inner surface 90 of the cover 72 and within the lower step 80. An outer diameter of the ram 106 may be smaller than an inner diameter of the through-hole 88 of the cover 72 such that there is no frictional engagement between the ram 106 and the cover 72. As shown in FIGS. 1-3, the ram 106 may be integrally formed with the shaft 32 and the thumb platform 30 such that the ram 106 is formed as part of the plunger assembly 37 in general. In some embodiments, the ram 106 may be formed with the thumb platform 30, and the thumb platform 30 may have a receiver portion that receives a proximal portion of the shaft 32.

In use, the braking mechanism 74 prevents the plunger assembly 37 from retracting toward the retracted position during operation of the syringe as long as the brake member 74 is maintained at the braking position. The user may release the thumb platform 30 without any concern that the plunger assembly 37 will be traversed back toward the refracted position. In some embodiments, various techniques may be used to regulate the translation of the plunger assembly, such as the techniques disclosed in concurrently filed application Ser. No. 12/842,844 entitled "RETRACTABLE SAFETY SYRINGE WITH NON-LOADED SEAL" and filed Jul. 23, 2010, the entire disclosure of which is expressly incorporated herein by reference.

Referring now to FIGS. 2-7, the retractable safety syringe 10 may be shipped and ultimately provided to a medical professional or user with the plunger assembly 37 in a retracted position (see FIG. 2) without fluidic medication contained within the variable fluid chamber 34. In the retracted position, the narrow portion 32b of the shaft 32 is proximate the shaft seal 92 and there is little or no vacuum in the vacuum chamber 12. Accordingly, there is essentially no load pressure on the various seals. The user may then distally traverse the plunger assembly 37 into the filling position. In the filling position, the brake member 74 remains in frictional contact with the inner surface 90 of the cover 72 and the wedge element 152 remains in frictional contact with the needle holder 18.

The vacuum chamber 12 is enlarged upon movement of the plunger assembly 37 toward the distal portion 20 such that the internal volume of the vacuum chamber 12 is increased. Since the vacuum chamber is sealed, the vacuum created within the vacuum chamber 12 may exert a retraction force upon the plunger assembly 37. As will be understood by one of skill, the refraction force may be exerted upon the shaft 32 indirectly via exertion upon the proximal surface of the proximal piston 28. The retraction force may vary as the plunger assembly 37 moves toward the distal portion 20 or toward the proximal portion 24. Thus, the refraction force may increase or decrease, respectively. The retraction force may be exerted on the plunger assembly 37 directed from the distal portion 20 toward the proximal portion 24. The retraction force may be caused due to a vacuum pressure in the vacuum chamber 12.

Figure 4:
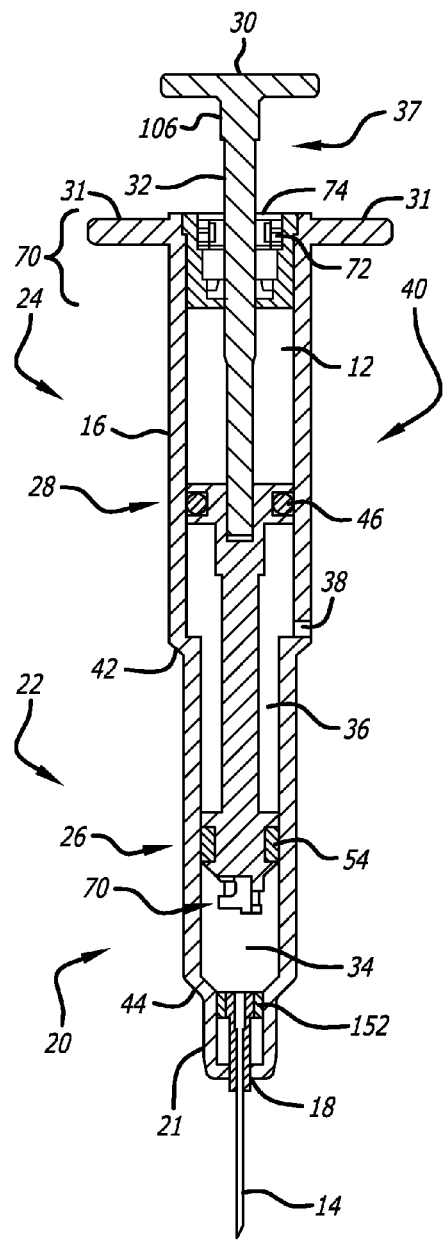
Figure 5:
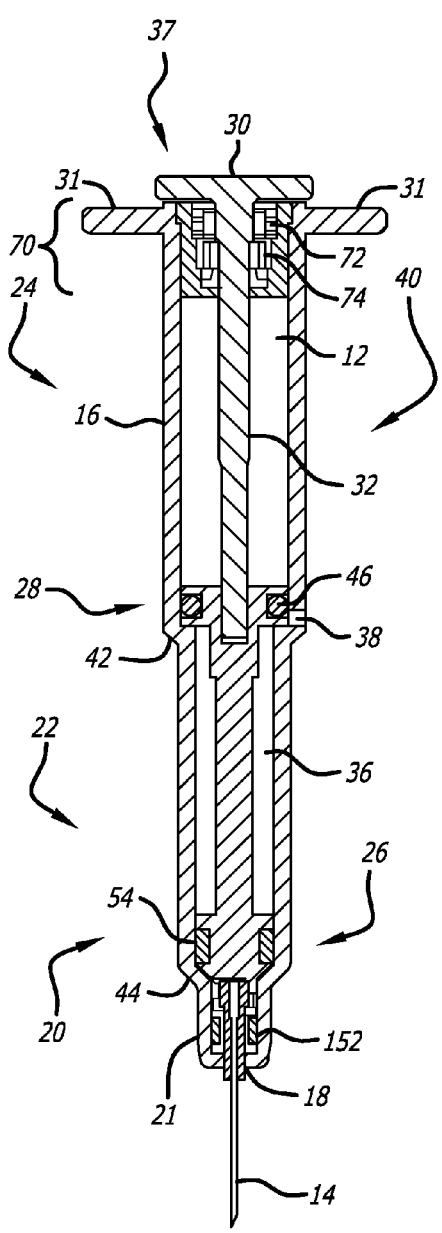

The intermediate chamber 36 is bounded distally by the distal piston 26 and proximally by the proximal piston 28. FIGS. 2, 4, and 5 illustrate the intermediate chamber 36 during various stages of operation, in accordance with one non-limiting embodiment. FIG. 2 illustrates when the intermediate chamber is 36 bounded by the proximal portion 24. FIG. 4 illustrates the intermediate chamber 36 being partially bounded by the proximal portion 24 and partially bounded by the intermediate portion 22. FIG. 5 illustrates when the intermediate chamber 36 bounded by the intermediate portion 22. In the illustrated embodiment, the inner diameter of the proximal portion 24 is larger than the inner diameter of the intermediate portion 22. As the plunger assembly 37 is moved toward the distal portion 20, the intermediate chamber 36 may decrease in volume. As the volume of the intermediate chamber 36 decreases, air from the intermediate chamber is expelled through the vent 38 in order to avoid a build-up of internal pressure. Conversely, as the plunger assembly 37 is moved toward the proximal portion 24, the intermediate chamber 36 may increase in volume. As the volume of the intermediate chamber 36 increases, air from a volume 40 external the intermediate chamber 34 is admitted through the vent 38 in order to avoid the creation of vacuum pressure.

When the retractable safety syringe 10 is in the filling position, the needle 14 may be inserted into a medication container containing fluidic medication. The medical professional or user may slip his or her fingers underneath the thumb platform 30 and pull the thumb platform 30 away from the syringe body 16. Note that even though the vacuum chamber 12 is exerting a vacuum force on the proximal piston 28 when the retractable safety syringe 10 is in the filling position, the force exerted by the brake member 74 on the shaft 32 exceeds the vacuum force. As the plunger assembly 37 is traversed toward the retracted position, the fluid within the medication container is transferred into the fluid chamber 34 via the needle 14. When the appropriate amount of fluidic medication is filled in the variable fluid chamber 34, the user stops traversing the thumb platform 30 away from the syringe body 16. The user or medical professional removes the needle 14 from the medication container. A small amount of air may be trapped within the variable fluid chamber 34. To remove the trapped air, the user or medical professional may invert the retractable safety syringe 10 such that the needle 14 is pointed upwardly. The user or medical professional taps the outside surface of the syringe body 16 to urge the trapped air within the fluid chamber 34 toward the needle tip. The medical professional or user may place his or her first and second fingers underneath the finger platforms 31 and place his or her thumb on the thumb platform 30. When the thumb platform 30 is depressed to remove the trapped air within the variable fluid chamber 34, a retraction force is created by the vacuum chamber 12 when the plunger assembly 37 is traversed toward the engaged position to remove trapped air within the variable fluid chamber 34. The force exerted by the brake member 74 on the shaft 32 exceeds the retraction force, thereby allowing the medical professional or user to remove their thumb from the thumb platform 30, if necessary.

At this moment, the retractable safety syringe 10 has been prepared to inject the fluidic medication into a patient. The needle 14 is inserted into the patient and the plunger assembly 37 is traversed from the retracted position to the engaged position. The user or medical professional traverses the plunger assembly 37 from the retracted position to the engaged position by placing his or her first and second fingers under the finger platforms 31 and his or her thumb on the thumb platform 30. As the vacuum chamber 12 is enlarged it produces a retraction force which urges the plunger assembly toward the retracted position. When the plunger assembly 37 is traversed to the engaged position, the distal piston 26 may engage the needle holder 18 and needle 14 (see FIG. 5). As the plunger assembly 37 is traversed to the engaged position, the ram 106 contacts the brake member 74 and pushes the brake member 74 out of the cover 72 and within the lower step 80 (see FIG. 3). With the brake member 74 pushed from the cover 72, the brake member no longer applies a braking force to the shaft 32.

Once the distal piston 26 engages the needle holder 18 and needle 14, the user or medical professional may release pressure on the thumb platform 30 such that the retraction force is greater than the thumb pressure and the plunger assembly 37 is urged back toward the retracted position (see FIG. 6). The needle holder 18 and needle 14 are urged back into the intermediate portion 22 of the syringe body 16 thereby covering the needle 14 and preventing accidental needle prickings and needle reuse. Also, the needle 14 may be canted toward one side of the syringe body 16. Canting the needle 14 toward one side of the syringe body 16 keeps the needle 14 from accidentally protruding through the distal end of the syringe body 16.

The distal piston 26 may be engageable to the needle holder 18 and needle 14 via any method known in the art. By way of example and not limitation, the distal piston 26 may be engageable to the needle holder 18 and needle 14 via the structure disclosed in U.S. Pat. No. 6,413,236, the entire content of which is expressly incorporated herein by reference.

Figure 8:
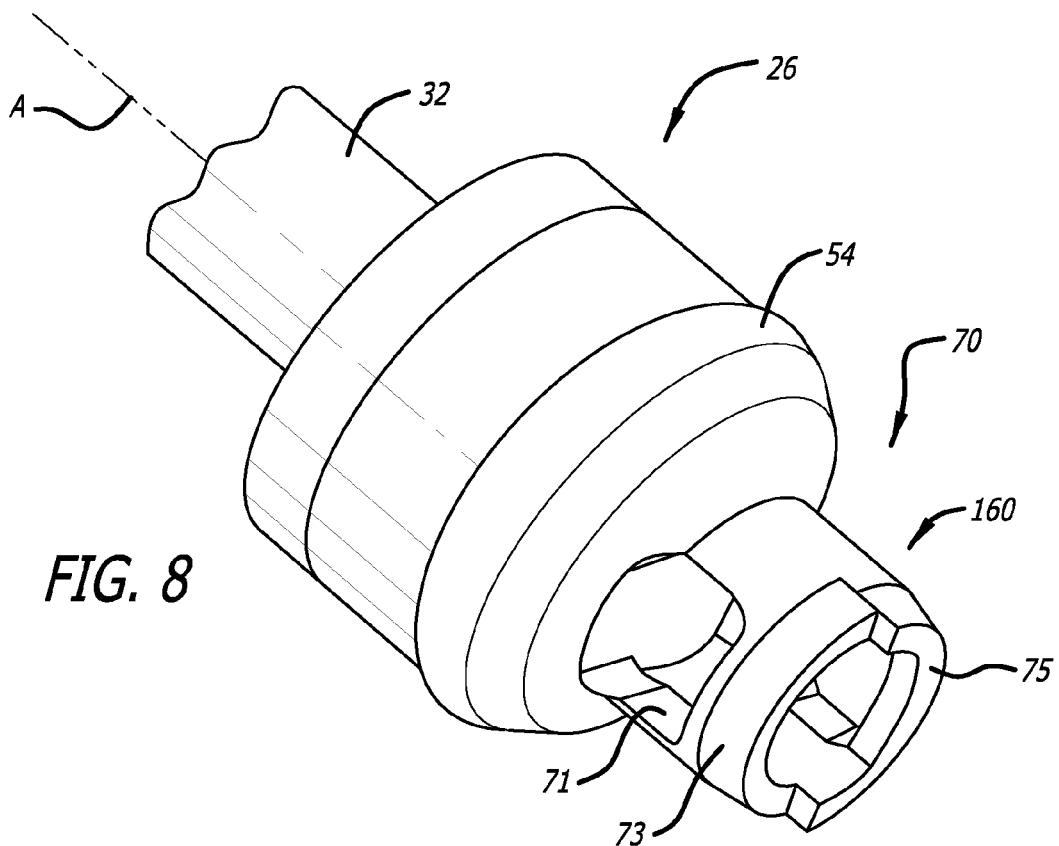
FIG. 8 is a perspective view of a distal piston of a retractable safety syringe in accordance with on non-limiting embodiment.
Figure 9:
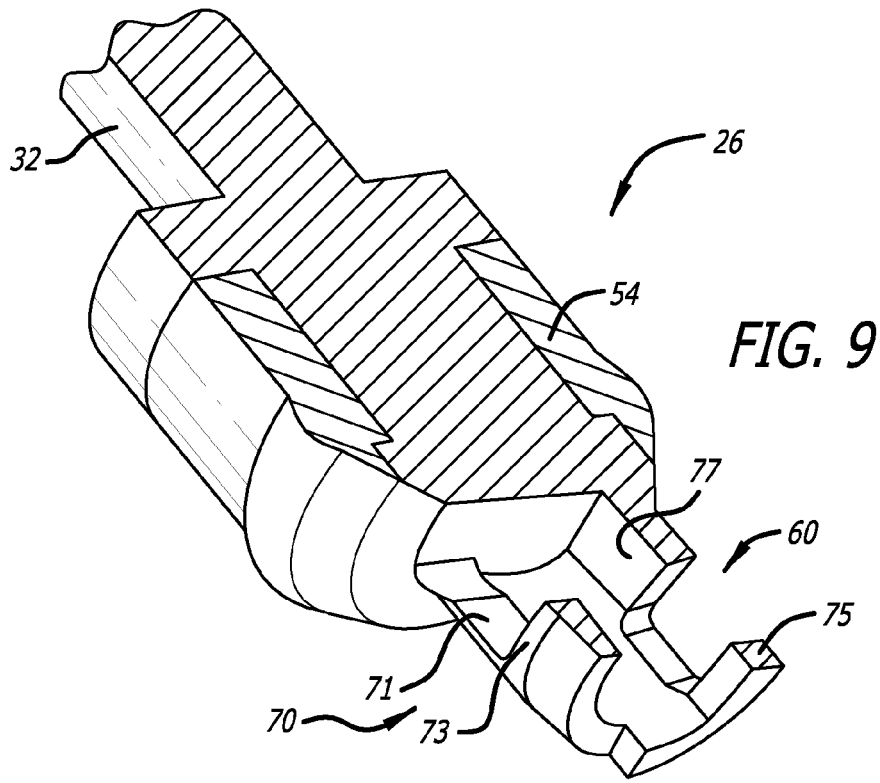
FIG. 9 is a cross-sectional view of the distal piston of FIG. 8.

FIG. 7 is an enlarged view of a portion of FIG. 6. FIG. 8 is a perspective view of the distal piston 26 in accordance with one non-limiting embodiment. FIG. 9 is a perspective view of the distal piston 26 of FIG. 8 taken along a longitudinal axis (illustrated as "A"). Referring now to FIGS. 7-9, by way of example and not limitation, the proximal portion of the needle holder 18 may have a step 19. The step 19 may be joined to a distal portion of the needle holder 18 via a lip 21. When the needle holder 18 is engaged to the distal portion 20, the wedge element 152 may be in frictional contact with the step 19 of the needle holder 18 (see FIG. 4). The distal piston 26 may have a punch 70 distally protruding toward the needle holder 18. The punch 70 may be a substantially hollow cylinder. In one embodiment the punch 70 is equipped with an upper proximal block tab 73 extending around less than about one-half of the circumference of the substantially hollow cylinder, and a lower distal wedge tab 75 extending around less than about one-half of the circumference of the substantially hollow cylinder and located opposite the upper block tab 73. During the engagement process, the punch 70 may distally push the wedge element 152 (see FIG. 5) and engage the needle holder 18, and more particularly, the lip 21 of the needle holder 18. The lower distal wedge tab 75 passes and hooks onto the lip 21 of the needle holder 18 when the plunger assembly 37 is traversed to the engaged position, as shown in FIG. 7. After engagement, the needle body 18 and needle 14 are withdrawn into the syringe body 16 via the retraction force. The punch 70 may also define a cutout 71 positioned longitudinally proximal to upper proximal block tab 73 and a ramp 77 (see FIG. 9) positioned longitudinally proximal to lower distal wedge tab 75. When the needle body 18 and the needle 14 are retracted, the ramp 77 may laterally bias the step 19 of the needle body 18 and the cutout 71 may receive a portion of the step 19 of the needle body 18 to cant (see FIG. 7) the needle 16 toward one side of the syringe body 16.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments.

The invention claimed is:

1. A vacuum-retractable safety syringe, the syringe comprising:
a syringe body defining a distal portion, an intermediate portion, and a proximal portion;
a proximal seal located in the proximal portion of the syringe body;
a plunger assembly disposed within the syringe body, the plunger assembly comprising a shaft, a distal piston, and a proximal piston, the plunger assembly being traverseable between a retracted position and an engaged position;
a needle coupled to a needle holder, the needle holder removeably engageable to the distal portion of the syringe body and engageable to the distal piston when the plunger assembly is traversed to the engaged position;
a fluid chamber disposed within the syringe body, the fluid chamber located distally from the distal piston, the fluid chamber having a distal and proximal end, the proximal end of the fluid chamber being sealed, the fluid chamber in fluid communication with the needle through the distal end of the fluid chamber and configured to be reduced in volume as the plunger assembly is traversed towards the engaged position;
a vacuum chamber disposed within the syringe body, the vacuum chamber located intermediate the proximal piston and the proximal seal, the vacuum chamber configured to provide a vacuum force on the proximal piston in a direction from the syringe body distal portion toward the syringe body proximal portion upon movement of the plunger assembly toward the syringe body distal portion responsive to the distal translation of the plunger assembly; and
an intermediate chamber disposed within the syringe body, the intermediate chamber located intermediate the distal piston and the proximal piston, the intermediate chamber having an air-passage vent connecting a volume external to the syringe body to the intermediate chamber when the plunger assembly is traversed between the retracted position and the engaged position.

2. The retractable safety syringe of claim 1, wherein the fluid chamber is a cavity having a first interior diameter, wherein the vacuum chamber is a cavity having a second interior diameter, and wherein the first interior diameter is smaller than the second interior diameter.

3. The retractable safety syringe of claim 1, wherein a volume of the intermediate chamber decreases when the plunger assembly is traversed between the retracted position and the engaged position.

4. The retractable safety syringe of claim 3, wherein when the plunger assembly is intermediate the retracted position and the engaged position, the intermediate chamber comprises a proximal portion having an inner diameter larger than an inner diameter of a distal portion of the intermediate chamber.

5. The retractable safety syringe of claim 1, wherein the intermediate portion has a first inner diameter, and the proximal portion has a second inner diameter.

6. The retractable safety syringe of claim 5, wherein the first inner diameter is less than the second inner diameter.

7. The retractable safety syringe of claim 6, wherein the outer diameter of the proximal portion is greater than the outer diameter of the intermediate portion, and wherein the retractable safety syringe further comprises a reducing portion coupling the intermediate portion and the proximal portion.

8. The retractable safety syringe of claim 7, wherein the air-passage vent is positioned proximal the reducing portion.

9. The retractable safety syringe of claim 1, wherein the proximal piston traverses the proximal portion when the plunger assembly is traversed between the retracted position and the engaged position.

10. The retractable safety syringe of claim 1, wherein the distal piston traverses the intermediate portion when the plunger assembly is traversed between the refracted position and the engaged position.

11. The retractable safety syringe of claim 1, further comprising an attachment base attached to the proximal portion of the syringe body, the attachment base having an in interior cavity defining an upper surface and a lower surface, the lower surface defining an attachment base inner diameter, wherein the attachment base is coupled to the proximal seal.

12. The retractable safety syringe of claim 11, wherein the plunger assembly comprises a thumb platform, wherein the portion of the shaft intermediate the thumb portion and the proximal piston comprises a distal shaft section having a first outer diameter and a proximal shaft section having a second outer diameter, wherein the first outer diameter is less than the second outer diameter, wherein the first outer diameter is less than the inner diameter of the lower surface of the attachment base.

13. The retractable safety syringe of claim 1, wherein the volume of the fluid chamber is less than 2 cubic centimeters when the plunger assembly is in the retracted position.

14. A vacuum-retractable safety syringe, the syringe comprising:
a syringe body defining a distal portion, an intermediate portion, and a proximal portion, wherein the distal portion has a first outer diameter, wherein the intermediate portion has a second outer diameter, wherein the proximal portion has a third outer diameter, wherein the first outer diameter is less than the second outer diameter, and the second outer diameter is less than the third outer diameter;
a needle coupled to a needle holder, the needle holder removeably engageable to the distal portion of the syringe body;
an attachment base attached to the proximal portion of the syringe body;
a plunger assembly comprising a proximal piston and a distal piston, wherein the proximal piston traverses the proximal portion when the plunger assembly is traversed between a retracted position and an engaged position; and wherein the distal piston traverses the intermediate portion when the plunger assembly is traversed between the refracted position and the engaged position;
a distal variable volume fluid chamber disposed between the needle and the distal piston;
an intermediate variable volume chamber disposed between the distal piston and the proximal piston, wherein the intermediate variable volume chamber has a vent connecting the intermediate variable volume chamber to a space external the syringe body; and
a proximal variable volume vacuum chamber disposed between the distal piston and the attachment base.

15. The retractable safety syringe of claim 14, wherein the volume of the distal variable volume fluid chamber is less than 2 cubic centimeters when the plunger assembly is in the retracted position.

16. The retractable safety syringe of claim 14, wherein the needle holder is engageable to the distal piston when the plunger assembly is traversed to the engaged position.

17. The retractable safety syringe of claim 14, wherein the distal piston has a first outer diameter and the proximal piston has a second outer diameter, and wherein the first outer diameter is less than the second outer diameter.

18. The retractable safety syringe of claim 14, wherein the distal piston and the proximal piston are separated by a distance along a longitudinal axis of the syringe body.

19. A method of operating an automatically retracting syringe, the method comprising:
receiving a vacuum-retractable syringe comprising:
a syringe body having first, second, and third cavities,
a needle coupled to a needle holder, the needle holder removeably engaged to the syringe body,
a plunger assembly comprising distal and proximal pistons, the plunger assembly disposed within the syringe body in a retracted position,
a vacuum chamber within the syringe body configured to urge the plunger toward the retracted position,
depressing a thumb platform to traverse the piston assembly toward a distal portion of the syringe during an injection stroke;
expelling air from the second cavity to a space external the syringe body through a vent;
inducing a gradually increasing biasing force on the proximal piston of the plunger assembly via the vacuum chamber to urge the piston assembly back toward the retracted position;
engaging the distal piston to the needle holder upon completion of the injection stroke;
disengaging the needle holder from the syringe body;
removing thumb pressure on the thumb platform; and
traversing the needle holder, and the needle into the syringe body under the biasing force.

20. A method of operating an automatically retracting syringe of claim 19, further comprising:
admitting air from the space external the syringe body to the second cavity through a vent when the needle holder, and the needle are traversed into the syringe body.

* * * * *